United States Patent [19]

Wang et al.

[11] Patent Number: 5,830,727
[45] Date of Patent: Nov. 3, 1998

[54] HERPES SIMPLEX VIRUS AMPLICON MINI-VECTOR GENE TRANSFER SYSTEM

[75] Inventors: Suming Wang; Charles J. Link, Jr., both of Des Moines, Iowa

[73] Assignee: Human Gene Therapy Research Institute, Des Moines, Iowa

[21] Appl. No.: 578,500

[22] Filed: Dec. 26, 1995

Related U.S. Application Data

[60] Provisional application No. 60/006,357 Nov. 8, 1995.
[51] Int. Cl.[6] .......................... C12N 15/389; C12N 5/10; C12N 15/86
[52] U.S. Cl. .................................. 435/172.3; 435/320.1; 435/364
[58] Field of Search .............................. 435/69.1, 172.1, 435/172.3, 240.2, 320.1, 364, 363, 366, 235.1

[56] References Cited

U.S. PATENT DOCUMENTS

| 4,970,155 | 11/1990 | Okasinski | 435/172.3 |
|---|---|---|---|
| 5,288,641 | 2/1994 | Boizman | 435/320.1 |

OTHER PUBLICATIONS

Orkin et al., "Report and Recommendations of the Panel to Assess the NIH Investment in Research on Gene Therapy", Dec. 7, 1995.

Geller, A., Nov. 1990, An Efficient Deletion Mutant Packaging System for Defective Herpes Simplex Virus Vectors: Potential Applications to Human Gene Therapy and Neuronal Physiology, *Proc. Natl. Acad. Sci. USA*, 87:8950–8954.

Glorioso, J., 1994, Development of Herpes Simplex Virus Vectors for Gene Transfer to the Central Nervous System, *Gene Therapeutics: Methods and Applications of Direct Gene Transfer*, Jon A. Wolff, Ed., Birkhäuser Boston.

Spaete, R., Feb. 1985, The Herpes Simplex Virus Amplicon: Analyses of CIS–Acting Replication Functions, *Proc. Natl. Acad. Sci. USA*, 82:694–698.

Miyanohara, A., Mar. 1992, Direct Gene Transfer to the Liver with Herpes Simplex Virus Type 1 Vectors: Transient Production of Physiologically Relevant Levels of Circulating Factor IX, *The New Biologist*, 4(3): 238–246.

Spaete, R., Aug. 1982, The Herpes Simplex Virus Amplicon: A New Eucaryotic Defective–Virus Cloning–Amplifying Vector, *Cell*, 30:295–304.

Hammerschmidt, W., 1988, Identification and Characterization of oriLyt, A Lytic Origin of DNA Replication of Epstein–Barr Virus, *Cell* 55:427–433, Kwong, A, Sep. 1984, Herpes Simplex Virus Amplicon: Effect of Size on Replication of Constructed Defective Genomes Containing Eucaryotic DNA Sequences, *Journal of Virology*, 51(3):595–603.

Johnson, P., May 1992, Cytotoxicity of a Replication–Defective Mutant of Herpes Simplex Virus Type 1, *Journal of Virology*, 66(5):2952–2965.

Geller, A., Sep. 1988, A Defective HSV–1 Vector Expresses *Escherichia Coli* β–Galactosidase in Cultured Peripheral Neurons, *Reports*, 1667–1669.

Frankel, Niza, Minireview: The Herpes Simplex Virus Amplicon–A Virsatile Defective Virus Vector, pp. S40–S46 (written with support of the Israel Cancer Research Foundation, and the Israel Academy of Sciences).

*Primary Examiner*—David Duzo
*Attorney, Agent, or Firm*—Zarley, McKee, Thomte, Voorhees, & Sease

[57] ABSTRACT

A novel HSV mini viral vector is disclosed. The vector comprises HSV and EBV genes which allow it to remain in episomal state, to have very high transfection and infection, and to tolerate up to 140 kb of foreign DNA. Techniques and genetic constructs for producing the vectors, for constructing the vectors and transfection and infection to recipient cells are disclosed.

33 Claims, 7 Drawing Sheets
(4 of 7 Drawing Sheet(s) Filed in Color)

HERPES SIMPLEX VIRUS AMPLICON MINI-VECTOR GENE TRANSFER SYSTEM

CROSS REFERENCE TO RELATED APPLICATION

This application claims benefit of earlier filed provisional application no.60/006357 filed Nov. 8, 1995 by Charles J. Link aid Suming Wang.

BACKGROUND OF THE INVENTION

The central focus of gene therapy is to develop methods for introducing new genetic material into somatic cells. To date two general classes of gene transfer methods have evolved. The first is DNA-mediated gene transfer and involves direct administration of DNA to the patient in various formulations. These methods use genes as medicines in a manner much like conventional organic or protein compounds. DNA-mediated gene transfer however has proven quite difficult. Methodology such as micro-injection, lipofection, and receptor mediated endocytosis have usually resulted in lower gene transfer, and usually establishes only transient residence of the novel gene in the targeted cell. Permanent incorporation of genes into cells occurs rarely after DNA-mediated gene transfer in cultured cells (less than $1 \times 10^5$ cells) and has not been significantly observed in vivo. Thus DNA-mediated gene transfer may be inherently limited to the use of genes as medicines that are administered by conventional parenteral routes to provide a therapeutic effect over predictable period of time. Studies of a therapeutic gene product may be constituted by repetitively dosing the patient with degenerate material much like conventional pharmaceutical medicines.

Viral gene transfer on the other hand involves construction of synthetic virus particles (vectors) that lack pathogenic functions which are incapable of replication, which contain a therapeutic gene within the viral genome and which deliver this gene to cells by the process of infection.

To date the viral vector which has achieved the most success and attention is a retroviral vector. The prototype for a retroviral mediated gene transfer is a retroviral vector derived from Moloney Murine Leukemia Virus. Retroviral vectors have several properties that make them useful for gene therapy. First is the ability to construct a "defective" virus particle that contains the therapeutic gene and is capable of infecting cells but lacks viral genes and expresses no viral gene products. The Moloney Leukemia Virus genome encodes the polyproteins gag, pol, and env that together constitute a retroviral particle. The gag and pol genes encode the inner core of the retrovirus as well as the enzymes required for processing the retroviral gene after infection of the target cell. The env gene forms the outer envelope of the virus and recognizes a specific receptor on target cells.

Retroviral vectors are capable of permanently integrating the genes they carry into the chromosomes of the target cell. Considerable experience in animal models and initial experience in clinical trials suggest that these vectors have a high margin of safety.

One limitation to these vectors is that a retrovirus will only integrate into actively dividing cells, making transduction into post mitotic or quiescent cells such as neurons or muscle impossible.

Murine retroviral vectors also have extremely inefficient in vivo gene transfer. Transduction efficiency is generally around 1–3% by direct injection of murine retroviral vector supernate in vivo. This efficiency of gene transfer has been somewhat improved by direct injection of murine retroviral vector producer cells (VPC) in vivo resulting in gene transfer efficiency of 10–60% but this efficiency is dependent on VPC titers and the number of VPC injected. Murine retroviral vectors are generally produced at low titer ($10^{5-6}$ cfu/ml), and large numbers of VPC injected into the human body can cause inflammation and repeated small amounts of VPC injection can induce an immune response that will likely prevent any further therapeutic effect. The third limitation of the vector is the size of insert. The maximum size of insert is about 7.5 kb which is not enough for larger CDNA such as the Duchennes Muscular Dystrophy gene (14 kb CDNA).

These vectors also insert their genes randomly into the host cell DNA and this random insertion may activate a proto-oncogene or inactive a tumor suppressor gene, causing safety concerns. The most perplexing problem however has been the difficulty in achieving stable regulated expression from retroviral vectors in cells that permanently carry these genes. The cells are apparently able to shut off expression from retroviral vectors under certain conditions.

Vectors based on adenovirus have recently proven effective as vehicles for gene transfer in vitro and in vivo in several cell types. Adenoviral vectors are constructed using a deleted adenoviral genome that lacks either the e-3 gene region and/or the e-1 gene region that is required for producing a replicating adenovirus particle. Recombinant genes are inserted into the site of the deleted gene region(s). Adenoviral particles are then produced in a cell line that is able to express e-1 or e-3 genes and thus capable of assembling a viral particle which contains only the recombinant viral genome with the therapeutic gene.

Adenoviral vectors differ from retroviral vectors in that they do not integrate their genes into the target cell chromosome. Adenoviral vectors will infect a wide variety of both dividing and non-dividing cells in vitro and in vivo with a high level of efficiency providing expression of their recombinant gene for a period of several weeks to months.

Current technology has enabled construction of adenoviral vectors that are incapable of proliferating however they are not completely "defective" and will express a series of viral gene products. Under certain conditions however adenoviral vectors remain capable of inducing cell lysis and an inflammatory response. The primary disadvantage of the adenoviral vector is the limited of capacity for the insert gene. The maximum capacity is for 7,000 base pairs of DNA. Also severe inflammation has been noticed during the experimental clinical trial for the treatment of cystic fibrosis.

Other viruses exhibit properties that may be useful as potential vectors for gene therapy. One such virus is the adeno-associated virus vector. It, like the retrovirus can provide a completely defective vector that permanently integrates in the chromosome of the target cell. This adenoviral vector integrates at a predictable location within the affected cell and could make this type of vector safer than those that integrate randomly into the genome.

Another promising viral vector is based on the Herpes Simplex virus. Herpes virus vectors are capable of infecting cells and persisting indefinitely in a latent state. Traditionally the herpes simplex virus vector involves genetic engineering of the viral genome to render it useful for serial propagation of the gene along with the viral genome and for sustained expression of foreign genes in a suitable host. Thus the entire viral genome becomes a vector for expression of the foreign gene in affected cells. This expression is then regulated by promoter regulatory regions present within the genome. The recombinant virus is difficult to handle and its capacity for insertion of exogenous DNA is limited to a range of 4.3 kb to 30 kb HSV-1 (Herpes Simplex Virus type 1). Although HSV-1 has relatively larger capacity for the insert, it is still under development and the apparent cytotoxicity has been observed due in part to toxicity of residual viral proteins produced by the virus. U.S. Pat. No. 5,288,641 to Roizman discloses use of the entire Herpes Simplex Virus as a vector vehicle, the disclosure of which is incorporated herein by reference.

As can be seen, there is a need in the art for a vector system which can be produced high titer which has a wide tropism, and which has a high efficiency of transduction.

It is an object of the present invention to provide a Herpes Simplex Virus mini-viral vector which is replication incompetent with a very high efficiency of transduction.

It is yet another object of the invention to provide a vector which is maintained in episomal form in transducted cells.

It is yet another object of the invention to provide a vector which is a plasmid form which is smaller and more easily handled than an entire Herpes Simplex Virus vector, and is capable of rolling circle replication.

It is yet another object of the invention to provide a vector which can tolerate up to 140 kb of foreign DNA.

SUMMARY OF THE INVENTION

The present invention provides techniques and genetic constructs useful for producing HSV mini-viral vectors conveniently and in large quantities. These and other aspects of the invention have been accomplished by providing the vectors, cells and methods of the present invention.

The invention comprises a HSV mini vector which combines a replication incompetent HSV amplicon with other viral sequences such as those from Epstein-Barr virus, human papillomavirus, or bovine papillomavirus type 1 which allow the vector to be maintained in the cell in episomal form achieving a 10 times greater titre, and a very large DNA insert capacity.

One embodiment of the present invention involves a helper virus-dependent mini-viral vector comprising: (a) the HSV-1 "a" sequence for the package/cleavage signal and an "ori S" replication origin for the replication packaging of the plasmid (in response to signals to replicate and package from the helper virus); (b) an Epstein-Barr virus (EBV) nuclear antigen (EBNA-1) gene and an EBV latent origin of replication (oriP) which allow the vector to be maintained in episomal form within the nucleus for replication without integration to the host genome and for even replication into each of two dividing cells; and preferably (c) genes from prokaryotic cells for propagation of the vector in E. coli (a selectable marker gene such as the ampicillin resistance or tetracycline resistance gene and the col. E1ori). Optionally the vector may also comprise prokaryotic genes that provide for a second selectable marker such as the genes for positive Hygromycin selection.

In this particular embodiment the packaging function of mini-vector DNA into Herpes simplex viral capsids is provided by a helper virus and a helper cell line.

In yet another embodiment the HSV vector can be engineered to produce a helper free viral vector as in Mann et al., "Construction of a Retro-Virus Packaging Mutant and its Use to Produce Helper-Free Defective Retrovirus", 33 Sal., p. 153–159, May 1983, Journal of Virology, September 1989, pp. 3822–3829, September 1989; Samulski "Helper Free Stocks of Recombinant Adeno-Associated Viruses: Normal Integration Does Not Require Viral Gene Expression"; and Kohn et al., "High Efficiency Gene Transfer Into Mammalian Cells: Generation of Helper-Free Recombinant Retrovirus With Broad Mammalian Host Range", PNAS, Vol. 81, pp. 6349–6353, October 1984. See also Okasinki, U.S. Pat. No. 4,970,155 "HSV HELPER VIRUS INDEPENDENT VECTOR", incorporated herein by reference.

The present invention further provides cells and cell lines comprising an HSV/EBV plasmid vector. Such cells or cell lines are useful in methods for producing this vector (pHE). Such methods, as provided by one helper dependent embodiment of the present invention, comprise the following steps.

Introducing into a helper cell line, the IE3 gene of HSV; or obtaining such an engineered cell line from a commercial source; introducing to said cell line the pHE plasmid vector of the present invention; growing the pHE particles in cells in growth medium; and inducing virion propagation with an IE3 deletion mutant helper virus. In a preferred embodiment prior to the virion propagation step, stable pHE cell transformants may be selected via hygromycin resistance.

DETAILED DESCRIPTION OF THE FIGURES

The file of this patent contains at least one drawing executed in color. Copies of this patent with color drawing(s) will be provided by the Patent and Trademark Office upon request and payment of the necessary fee.

FIG. 1 is a depiction of the plasmid vector pHE700 one embodiment of the invention. AmpR ampicillin resistant gene; "a" is a HSV-1 packaging signal; tk promoter is a Herpes simplex virus thymidine kinase promoter gene; hyg+ is a hygromycin resistance gene; tk poly A is a Herpes simplex virus thymidine kinase polyadenylation signal; SalI is a restriction site; CMV is the human cytomegalovirus promoter; MCS is a multi-cloning site for insertion of exogenous DNA; SV40 poly A is the E. coli SV40 polyadenylation signal; SalI is a second restriction site; RSV promoter is a Rous sarcoma virus promoter; EBNA-1 is the Epstein-Barr virus gene encoding the EBV nuclear antigen EBNA-1; ORI P is the Epstein-Barr virus unique latent replication origin; ori S is a Herpes simplex virus replication origin for replication of the plasmid; and col E1 is the E. coli gene for propagation in E. coli cells.

FIGS. 4(a)–4(d) depict photographs of pHE 700-lac virus stock which was used to infect VA13 normal fibroblasts at a MOI of 3 (FIG. 4A), SV3 CRL 9.7 xeroderma pigmentosum fibroblasts at an MOI of 10 (FIG. 4B), IGROV human ovarian carcinoma cells at an MOI of 10 (FIG. 4C), and a human glioblastoma cells at an MOI of 10. (FIG. 4D).

DETAILED DESCRIPTION OF THE INVENTION

According to the current invention, a nucleotide sequence, the expression of which is desired in a particular cell, is inserted into a plasmid HSV/episomal vector for expression of the foreign gene in infected cells. This type of HSV vector has important clinical applications for in vivo or ex vivo gene therapy, particularly due to the neurotropism of the HSV virus. HSV can infect virtually any type of cell, however its ability to infect neural cells opens new applications for gene therapy.

Currently most neurodegenerative diseases are not treatable. Even in cases where therapies exist, drugs which control symptoms may ultimately fail in the late stages of neurological disease in a considerable percent of affected patients. For example the administration of L-dopa to Parkinsons patients has been found to even accelerate the decline in dopamine producing neurons.

Other difficulties with traditional therapies are the blood brain barrier limitation of the delivery of systematically administered drugs to the brain parenchyma and even drugs delivered by interventricular injection penetrate poorly from the ventricular surface into the substance of the brain.

Direct targeting of therapeutic product to specific brain regions or to cells within those regions may be required to overcome these limitations. As an alternative to targeted drug delivery neurodegenerative diseases may be treated by gene therapy where direct gene transfer to the effected gene region will accomplish local therapeutic gene product synthesis. Recessive metabolic diseases of the nervous system caused by defects in single genes potentially could be cured by replacement of the defective gene with a correct gene. Multifactorial neurodegenerative conditions might be ameliorated by the production of therapeutic products from transferred genes.

In addition animal models of human disease like Alzheimer's might be produced by transgene overexpression of potentially pathogenic proteins such as normal or mutant forms of the amyloid precursor protein. Such animal models could be used to both explore the role of those substances in the pathogenesis of disease as well as to test the effects of potential therapeutic agents. Finally gene transfer holds considerable promise for the treatment of acquired disease processes effecting the nervous system such as autoimmune degeneration of white matter, cancer and brain scarring due to injury. Retroviral vectors which have successfully been exploited in the transfer of genes to bone marrow derived cells, fibroblasts and neoplastic cells cannot be used to transfer genes directly into the brain because these vectors require cell division for incorporation of the therapeutic recombinant vector into the cellular genome and neurons are post-mitotic.

Herpes simplex virus type 1 is transmitted by direct contact and replicates in the skin or mucous membranes before invading the peripheral nervous system. The virus can enter a latent state in which the latent genes rather than the lytic genes are expressed and the virus does not replicate. The viral genome can persist in this state for the life of the host or may be reactivated to re-enter the lytic cycle and cause a secondary infection usually at the primary site.

The HSV virus can be forced into "latency" in any cell type by removal of the immediate early lytic gene functions. Such defective HSV vectors can be propagated on cell lines which express the deleted essential functions in trans. These complementing cell lines are capable of producing defective virus to high titers without wild type recombinants which highlights the safety of these defective vectors.

Finally latent viral genomes exhibit characteristic and restricted pattern of expression of RNA transcripts implying that latency active promoters exist and can be exploited to express foreign genes in the latent viral genome.

HSV-1 is a large, enveloped, double-stranded DNA virus that is composed of approximately 152 kb encoding 75 genes. The nucleotide sequence of HSV-1 is disclosed in McGeoch, D. et al., *J. Mol. Biol,* 1985, 181:1–13, Nucleic Acids Research, 1986, 14:1727–1745; *J. Gen. Virol,* 1988, 69:1531–1574; and *J. Gen. Virol,* 1988, 69:2831–2846, all of which are incorporated herein by reference. Herpes simplex virus 1 is also readily available to the public. It is, for example, on deposit with the American Type Culture Collection, 12301 Parklawn Drive, Rockville, Md. 20852, USA, under ATCC accession number VR733. The DNA of Herpes simplex virus type 2 (HSV-2) is essentially identical in structure to that of HSV-1 and differs only in nucleotide matching of base pairs. Therefore DNA constructs identical to those illustrated herein using the HSV-1 genome are feasible according to the present invention.

Viruses that infect eukaryotic cells often specify regulatory proteins to insure the appropriate expression of genes during the viral life cycle. HSV encodes several proteins that directly modulate viral and cellular gene expression and mediate the complex temporal cascade exhibited by the different transcription units in the HSV genome. This cascade unfolds in three phases of coordinated gene expression. Immediate early (IE) early (E) or late (L). One IE protein, ICP4 is required for viral infection to proceed past the IE phase of transcription and is therefore absolutely essential for virus growth. ICP4 function can be eliminated by genetically altering the two copies of ICP4 gene in the viral genome. Suitable procedures for insertion and deletion of genes are known to those of skill in the art and are disclosed for example in Maniantis, "Molecular Cloning" Cold Spring Harbor Press. See also, Post et al., *Cell,* Vol. 24, pp. 555–565 (1981).

The isolation and propagation of such mutants in cell culture requires that complementing levels of the ICP4 protein be provided in trans. Thus the invention in one embodiment contemplates a method using a helper cell line which has been transformed to express a complementing IE gene such as IE3 as well as an HSV amplicon which has no such IE3 gene and is replication incompetent. Further deletions from the HSV genome have made for much smaller vectors, which when combined with a helper virus supplying the propagation and gene expression functions, can be packaged into virions.

These sort of replication incompetent HSV amplicons have been constructed in the art, one example is the pHS-Vlac vector by Geller et al, *Science,* Vol. 241, Sept. 1988, incorporated herein by reference. These HSV amplicons contain large deletions of the HSV genome to provide space for insertion of exogenous DNA. Typically they comprise the HSV-1 packaging site, the HSV-1 "ori S" replication site and the IE 4/5 promoter sequence. These virions are dependent on a helper virus for propagation.

HSV-1 vectors have been propagated in a virus stock with wild-type HSV-1 as helper virus, however the wild-type HSV-1 virus invariably caused cell death. Primarily two types of mutant helper viruses have been developed to combat this problem. Other complementary HSV helper virus systems are contemplated herein and are within the scope of those of skill in the art. One such system which has been developed is a temperature-sensitive mutant. An HSV temperature-sensitive (TS) mutant has been developed with a TS mutation in the IE3 gene. Davison et al, 1984, *J. Gen. Virol.,* 65:859–863. Consequently this virus has an IE phenotype, does not replicate DNA, does not significantly alter cellular physiology, and does not produce progeny virus at 37° C. Virus is grown at the permissive temperature of 37° C. TS mutants however have had a tendency to revert to wild type.

In contrast a second helper virus system is a deletion mutant with the majority of the IE3 gene simply deleted. These do not revert to wild type. Therefore HSV-1 vectors packaged using a deletion mutant as helper virus is the most preferred helper virus of the invention. See for example Patterson et al., 1990, *J. Gen. Virol.*, 71:1775–1783. Other replication incompetent helper viruses can be used and one of skill in the art will appreciate that other mutations in the IE genes or other genes which result in a replication incompetent helper virus which will provide the appropriate replication and expression functions and which are coordinated with the helper cell line and vector are contemplated within this invention.

Thus the invention contemplates a method for packaging of a plasmid helper dependent HSV replicon by the following steps. Transforming a helper cell line to express the HSV IE3 gene or other complementary replication dependent HSV gene. Any cell line can be used for this step so long as it is capable of expressing the IE3 or replication dependent gene, or obtaining a helper cell line which has already been transformed and is commercially available. Any cell line can be used by introducing pHE and the plasmid containing the IE3 gene simultaneously. Next, the vector is delivered to the helper cell line by electroporation, calcium phosphate DNA transfection or any other suitable method. Any cell line can be used by introducing pHE and the plasmid containing the IE3 gene simultaneously. The cells are next infected with a helper virus IE3 deletion mutant or other corresponding deletion mutant which is replication incompetent. The IE3 gene or other such gene in the helper cell line complements the helper virus resulting in a productive HSV-1 infection and the resulting virus stock consists of HSV-1 particles containing either vector DNA or helper virus DNA, all of which are replication incompetent. Further information about helper cell lines and the methodology is disclosed in Geller et al., PNAS, 87:8950–8954, November 1990, "An Efficient Deletion Mutant Packaging System for Defective Herpes Simplex Virus Vectors: Potential Applications to Human Gene Therapy and Neuronal Physiology".

THE HSV/EBV VECTOR

In one embodiment the mini-viral vector of the invention can replicate and be packaged in the multimers form in presence of Herpes simplex virus helper virus and helper cell line. The vector contains elements from the Herpes simplex virus which provides the sequence for the package/cleavage signal and the replication origin for the replication and packaging of the plasmid in response of the signal of replication of helper virus. It also contains elements from other virus which allow the vector to be maintained in episomal form. For example Human papillomavirus type 16, Sabbioni S., "A BK Virus Episomal Vector for Constitutive High Expression of Exogenous cDNAs in Human Cells", *Arch Virol*, (1995) 140(2):335–9; Tidy, J., "A Novel Deletion Within the Upstream Regulatory Region of Episomal Human Papillomavirus Type 16", *J Gen Virol*, (April 1989) 70 (Pt 4)(Pt 4):999–1004; Manservigi, R., "Protection From Herpes Simplex Virus Type I Lethal and Latent Infections by Secreted Recombinant Glycoprotein B Constitutively Expressed in Human Cells With a BK Virus Episomal Vector", *Virol* (Jan. 1990) 64(1):431–6; Milanesi, G., "BK Virus-Plasmid Expression Vector That Persists Episomally in Human Cells and Shuttles Into Eschericliia Coli", *Mol Cell Biol* (Aug 1984) 4(8):1551–60; Di Luca, D., "Episomal HPV 16 DNA Isolated From a Cervical Cercinoma Presents a Partial Duplication of the Early Region", *Virus Res* (Sep 1989) 14(1):49–55, and bovine papillomavirus type 1, Bergman P., et al., "Replication of the Bovine Papillomavirus Type 1 Genome; Antisense Transcripts Prevent Episomal Replication", *Gene* (1986) 50(1-3):185–93; Rosl, F., "Topological Properties of Bovine Papillomavirus Type 1 (BPV-1) DNA in Episomal Nucleoprotein Complexes: A Model System for Chromatin Organization in Higher Eukaryotes", *Mol Carcino*, (1991) 4(3):249–56, all of which are incorporated herein by reference, or the EBNA-1 sequence from Epstein-Barr virus. In one embodiment the vector contains the orip and EBNA-1 elements from Epstein-Barr virus. The EBNA-1 sequence helps maintain the vector in episomal form. It is the combination of elements from other Epstein-Barr virus with the HSV genome to enhance stability by maintaining the vector in episomal form which offers the primary advantage of the vectors of this invention. The mini-viral vector is in plasmid form which is easier to handle in comparison with other vectors which use the entire HSV genome. Additionally the mini-vector has multiple copies of the inserted gene in the packages form, thus single virions provide at least 10-fold more gene activity than traditional HSV using the entire HSV genome. The insert capacity of exogenous DNA is also a primary advantage allowing up to 140 kb. This can allow for insertion of very large genes such as Duchennes muscular dystrophy gene and also for insertion of not only the gene but also its own regulatory elements including enhancers and promoters as well as its exon, intron and terminal sequence regions.

The vector can even incorporate retroviral sequences for insertion into genomic DNA, or adenoviral or adeno-associated viral elements. The vector could also contain a large fragment of mammalian or other DNA for homologous recombination with genomic DNA and correction of defective genes including mutation, deletion, amplification etc. This embodiment could also be used to create a new hybrid animal.

The HSV genome contains three origins of replication, one located with the unique long segment (ori L) and two within the repeats flanking the unique short segment (ori S). By using the plasmid containing an HSV lytic origin of replication and a HSV terminal packaging signal sequences, it has been demonstrated that the plasmid or amplicon was amplified and packaged into infectious HSV virions in the presence of transacting wild type helper virus. The virions contained multimeric forms of the original monomeric vector by a rolling-circle replication mode.

Epstein-Barr Virus (EBV) is another member of human herpes virus family. EBV has been demonstrated to contain a unique latent replication origin (orip) which makes the virus self-replicate and stay in cells without entering the lytic cycle. The orip in the vector of this invention allows for episomal replication and maintenance in the cells expressing the EBV nuclear antigen EBNA-1, the only viral encoded binding transactivator for oriP. The vector may be maintained in episomal form in the cells for at least 6 months. The EBV viral genome has been fully sequenced and is commercially available through the American Type Culture Collection, Rockville, Maryland. See also Kioyssis D, "Expression and Rescuing of a cloned Human Tumour Necrosis Factor Gene Using an EBV Based Shuttle Cosmid Vector", EMBO (1987), 6:355–361; Rawlins et al., *Cancer Cells*, (1986), 4:525–542: Yates et al., *Nature*, (1985), 313:812–815. For example plasmid p220.2 contains the gene encoding EBNA and the EBV oriP DNA fragment which serves as the latent origin of replication of the virus (Yates et al., "Stable Replication of Plasmids Derived from Epstein-Barr Virus in Various Mammalian Cells", *Nature*, 313:812–815 and Sugden et al., "A Vector That Replicates as a Plasmid and Can be Efficiently Selected in Blymphoblasts Transformed by Epstein-Barr Virus", *Mol. Cell. Biol.,* 5:410–413). The plasmid also contains the hygromycin B resistance gene to allow selection of transformants with high frequency.

All DNA manipulations and plasmid constructions disclosed herein were performed using standard procedures known to those of skill in the art and are discussed in detail in the references disclosed and incorporated herein.

The vectors of the invention comprise HSV sequences for the package cleavage signal ("a") and the "ori S" replication origin with Epstein-Barr Virus (EBV) sequences EBNA-1 and "ori P".

In a preferred embodiment the vector also comprises sequences that allow propagation of the virus in *E. coli*: a selectable marker such as the ampicillin resistance gene or tetracycline, kanamycin, or zeocin gene or any other resistance gene and the E. col EI ori.

In a more preferred embodiment the vector comprises genes from prokaryotic cells or eukaryotic cells such as dihydrofolate reductase, or multi drug resistance-1 gene, hygromycin B resistance that provide for positive selection. Any type of positive selectable marker can be used such as neomycin, or zeocin can be used and these types of selectable markers are known in the art. This vector allows for much more efficient viral packaging in the helper cell line providing for selection of stably transformed helper cells before infection with the helper virus. An entire transcription unit must be provided for the selectable marker genes (hgy+) and the genes must be flanked on one end with a promoter-regulatory region and on the other with a transcription termination signal (polyadenylation site).

Any known promoter/transcription termination combination can be used with the hyg+ genes for example $SV_{40}$ promoter and $SV_{40}$ poly A.

Preferably the combination is the HSV-1 tk promoter and tk poly A region. This combination is widely used.

A foreign gene to be expressed can then be introduced into the vector of the invention. The foreign DNA can comprise an entire transcription unit, promoter-gene-poly A or the vector can be engineered to contain promoter/transcription termination sequences such that only the gene of interest need be inserted. These types of control sequences are known in the art and include promoters for transcription initiation, optionally with an operator along with ribosome binding site sequences. Examples of such systems include beta-lactase (penicillinase) and lactose promoter systems, (Chang et al., *Nature,* 1977, 198:1056); the tryptophan (trp) promoter system (Goeddel, et al., *Nucleic Acid Res.,* 1980, 8:4057) and the lambda derived Pl promoter and N-gene ribosome binding site (Shimatake et al., *Nature* 1981, 292:128). Other promoters such as cytomegalovirus promoter or Rous Sarcoma Virus can be used in combination with various ribosome elements such as SV40 poly A. The promoter could also be an inducible promoter tissue specific promoters, synthetic promoter containing promoter enhancer elements (Salk Institute). These types of sequences are well known in the art and are commercially available through several sources, ATCC, Pharmacia, invitrogen, Stratagene, Promega.

In a most preferred embodiment the vector comprises a specifically engineered multi-cloning site within which several unique restriction sites are created. Restriction enzymes and their cleavage sites are well known to those of skill in the art.

Figure 1:
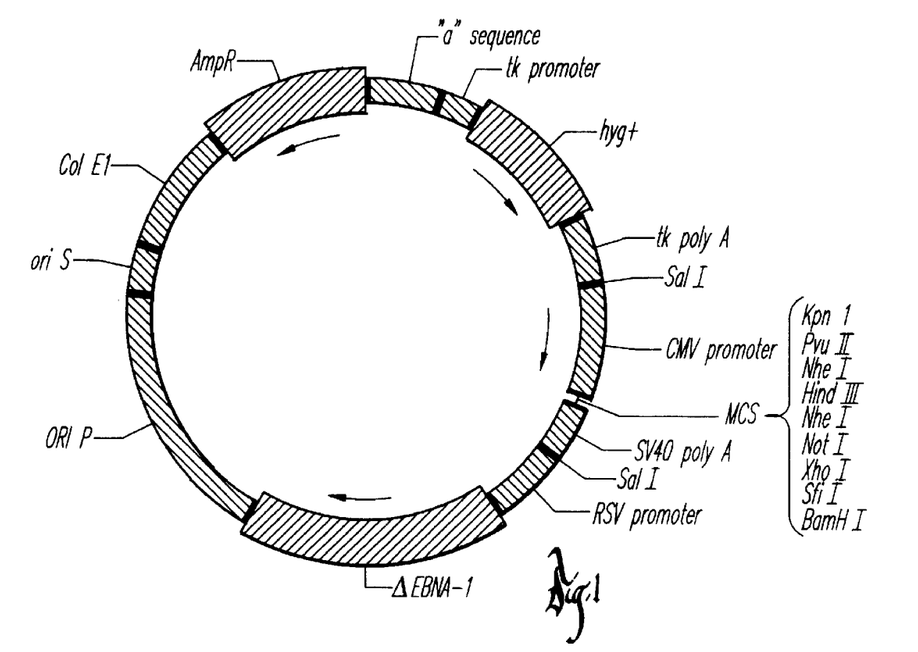
Figure 2A:
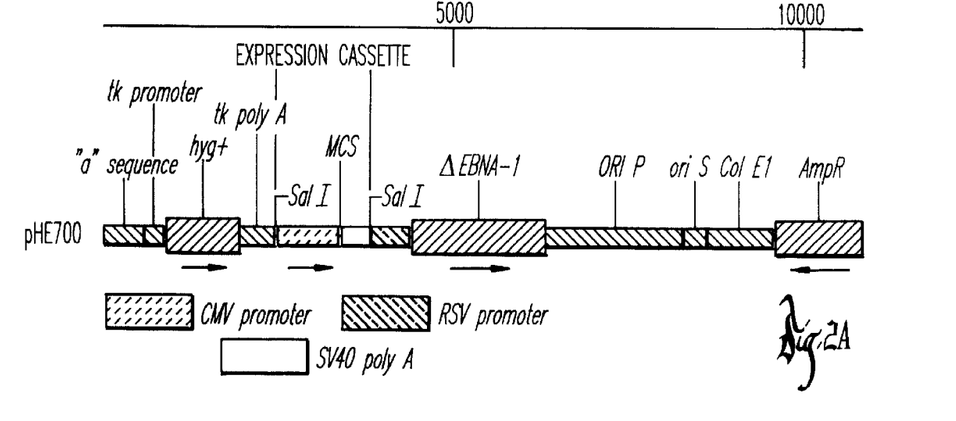
FIGS. 2(a)–2(h) depict several embodiments of HSV mini-viral vectors constructed according to the invention.
Figure 2B:
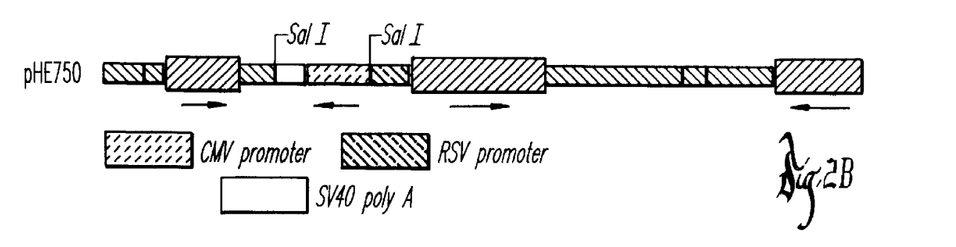
Figure 2C:
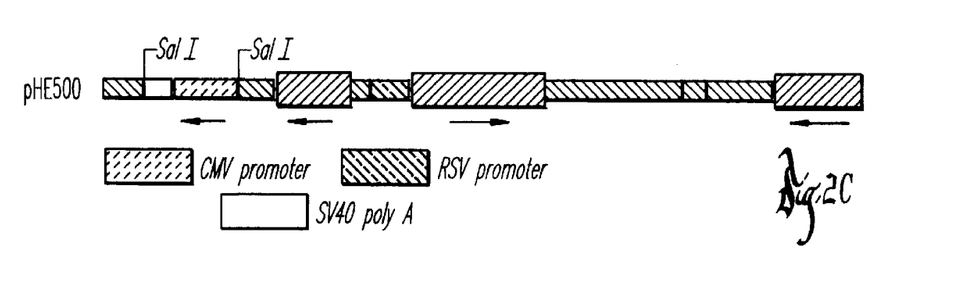
Figure 2D:
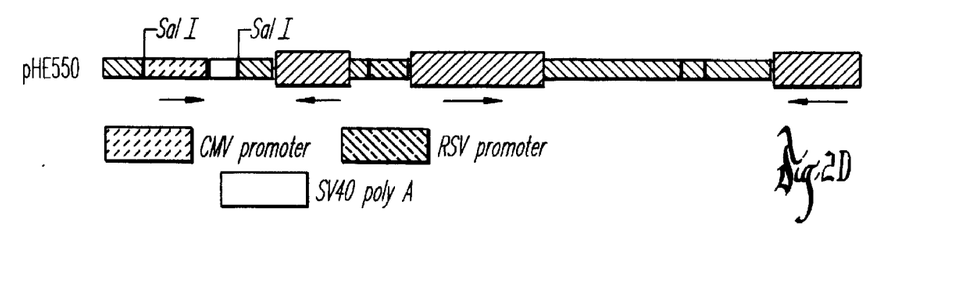
Figures 2E, 2F:
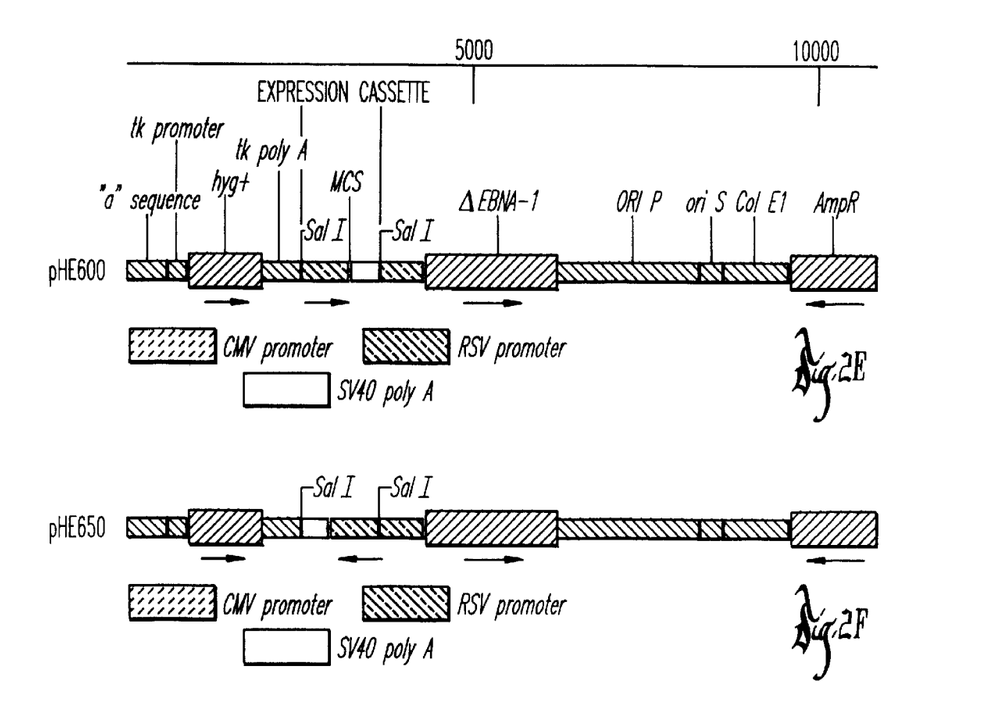
Figure 2G:
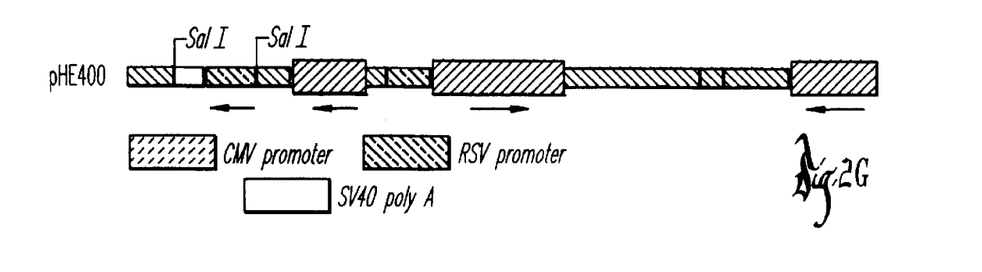
Figure 2H:
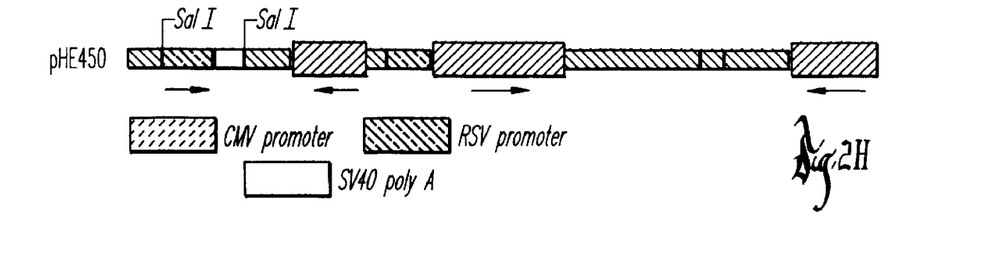

The vectors of the invention are demonstrated by an embodiment comprising the lac-Z gene. This is one example of the invention and in no way is intended to be limiting. A novel HSV-EBV based mini-viral vector, pHe, for the high efficiency transfer LacZ gene into various human cells in vitro and in vivo was developed. See FIG. 1. The vector contains the HSV replication origin, oriS and a HSV packaging sequence, "a", which make the vector be replicated and packaged in the presence of helper virus and helper cells, E5 that contain the IE3 gene for complementation. The latent replication origin, oriP and the transacti17ator, EBNA-1 derived from EBV allow the vector episomal maintaining the E5 cells so that the high titer of viral stocks can be made. pHE-lac has the lac-Z gene expressing β-galactosidase under the control of the human cytomegalovirus (CMV) immediate early promoter or Rous sarcoma virus (RSV) long terminal repeat (LTR) sequence. The β-galactosidase expression in infected cells including a number of tumor cells has been demonstrated. The efficiency of infection can be as high as 95 to 100% in cultured human fibroblast cells and epithelial cells without cytotoxicity.

Several plasmids were constructed according to the invention. Plasmids, pHE serials (pHE400; pHE450; pHE500; pHE550; pHE600; pHE700; pHE750), each of these embodiments contains basically three parts: a) the genes from Herpes simplex virus which provide "a" sequence for the package/cleavage signal and an "oriS" replication origin for the replication of the plasmid (in response to signals to replicate and package from the helper virus). b) Genes from the Epstein-Barr virus that allows for the vector to be maintained in episomal form within the nucleus. c) Genes from prokaryotic cells that provide for positive Hygromycin selection an(i the genes for amplification in bacteria, The packaging function of mini-vector DNA into Herpes simplex viral capsids is provided by both of the vector (in pHE) and by helper virus and the helper cell line.

The helper virus dependent mini-viral vectors of the invention are developed for easier operation and their capacity for insertion are theoretically as large as to the size of the original virus genome on which the vector is based. The mini-viral vectors contain the cis-acting viral elements required for their replication and packaging as infectious virions but they are totally defective for viral production and are thus dependent on a helper virus to provide the missing viral proteins in trans. The mini-viral vector combines the advantages of a plasmid's easy handling and virus's high efficiency of transferring by infection. The capacity for a large insert makes the vector be able to carry full length fragment of DNA and the functional expression will be controlled by its own endogenous elements. The mini-viral vector can also be designed for the desired mode of action by assembling several elements from different virus, therefore, creating a hybrid mini-viral vector system.

EXAMPLES

METHODS

Construction of pHE series of vectors and pHE700-Lac pHE is a series of plasmid constructs that are based a combination of Herpes simplex (H) and Epstein-Barr virus characteristics (E). The pHE700 plasmid is a 10,617 bp plasmid was generated from the combination of components from several other plasmids. Plasmid pTO11 (kindly provided by Dr. N. Stow, MRC, Glasgow, UK) was the source for the Herpes simplex virus (HSV) "a" packaging signal and the origin of replication, "oriS". The first step was to restrict plasmid pTO11 with Nsp I. The resulting plasmid was re-ligated after removing the Nsp I fragment containing the tetracycline resistance gene to form PTO11-NspI. Plasmid p500 (kindly provided by Dr. Hayakawa, Dept. of Biochemistry, Kyushu Univ., Fukuoka) was then restricted with Xmn I and Hind III, and the fragment containing the EBNA-1 sequence was ligated to a Xma 1 and Hind III fragment of PTO11-Nsp I that contained the "a" sequence. The resulting plasmid p501 then contained the "a" sequence. Plasmid p501 was restricted with Xho I and Xmn I and the resultant fragment containing the "a" sequence was ligated to a Xmn I and Cla I restricted fragment of p205 (kindly provided by Dr. Sugden, Univ. of Wisconsin) that provided the ΔEBNA-1 gene. This Δ EBNA-1 gene sequence is a modified version of the native EBNA-1 sequence which has less cytotoxicity compared to original EBNA-1 gene (personal communication from Dr. Sugden). The resultant plasmid was named p206.

Plasmid p206 was restricted with Nar I and Hind III and the fragment containing the ΔEBNA-1 (driven by the RSV promoter) and oriP was ligated to pTO11Nsp I restricted with Hind III and Bam HI (containing the "a" sequence and oriS). The resultant plasmid was termed pHE100. Plasmid pHE100 was then restricted with Hind III and this was ligated to a Xba I and Nru I fragment from pREP10 (purchased by Invitrogen Corp.) containing the hygromycin resistance gene and the multi-cloning site (MCS). Two resulting vectors were obtained pHE400 (the hygromycin expression cassette oriented 3'to 5') and pHE600 (the hygromycin expression cassette oriented 5'to 3') [See FIG. 3(a)–(h)]. Both plasmids pHE400 and pHE600 were then restricted with Sal I. This digest results in the restriction of a fragment containing just the RSV promoter, MCS, and polyA sequence. Self ligation after restriction allowed for the selection of plasmids, termed pHE450 and pHE650 respectively (See FIG. 3) with the cassette oriented in the 5'to 3' direction.

These same two plasmids (pHE400 and pHE600) were again restricted with Sal I and the large fragment was isolated and then ligated to the Sal I fragment of pCEP4 (purchased from Invitrogen Corp.) containing the CMV promoter expression cassette. For each restriction digest two resultant plasmids were cloned (See FIG. 2). For pHE400 the resulting plasmids were pHE500 (CMV cassette in 3' to 5'orientation) and pHE550 (CMV cassette in 5' to 3' orientation). For pHE600 the resulting plasmids were pHE700 (CMV cassette in 5' to 3' orientation) and pHE750 (CMV cassette in 3' to 5' orientation). pHE700-lac was constructed by inserting a lacZ gene into Hind III and Not I sites of multiple cloning sites of pHE700. The lacZ gene was from Hind III-Not I fragment of pCDMV3-lac (kindly provided by Dr. H. Takebe, Kyoto University, Japan). Plasmid pHE700-GFP was constructed by cloning Sal I and Xpa I fragment from the pGFP1 (Clonetech Corp) plasmid containing the GFP gene into the pHE700 MCS.

Cells and Viruses

All cells were grown and maintained in DMEM (GibcoBRL) containing 10% fetal bovine serum (FBS, Gibso), glutamine and penicillin/streptomycin, and incubated at 37° C. in a humidified, 5% $CO_2$ incubator. E5 is helper cells derived from African green monkey cells (Vero) and incorporated with IE3 gene of HSV in cell genome (kindly provided by Dr. Neal A. DeLuca, University of Pittsburgh). The cells were maintained with 400 mg/ml G-418 (Geneticin®, Gibco BRL). VA13 is SV40 transformed human WI38 cells. SV3 CRL 9.7 is SV40 transformed skin fibroblast cells derived from xeroderma pigmentosum patient, group variant, an inherited DNA repair defective disease (kindly provided by Dr. Marila Cordeiro-Stone, Univ. of North Carolina). T98G is fibroblast-like cells derived from human glioblastoma. IGROV is a human ovarian carcinoma cell line.

The virus were grown and titered in E5 cells. The HSV-1 strain 17+IE3 deletion mutant D120 (kindly provided by Dr. Neal Deluca, University of Pittsburgh) used as helper virus.

Transfection and Selection for Hygromycin Resistant

Transfection of pHE700-lac into E5 cells was carried out with Lipofection according to manufacture's recommendations (GIBCO BRL/Life Technologies, Gaithersburg, Maryland). Optimal result was determined by using 1 μg of plasmid DNA and 10 μg Lipofection, each diluted in 100 μl Opti-MEM media (GIBCO BRL/Life Technologies), mixed well and incubated at room temperature for 15 minutes. The lipsome-DNA complex was added to 5×105 actively growing E5 cells (washed previously in Opti-MEM media) in 2 ml of Opti-MEM in a six-well plate (Falcon, Lincoln Park, N.J.). The Opti-MEM was replaced with complete medium after the cells were incubated for 12–15 hours at 37° C. in a humidified, 5% $CO_2$ incubator. Two days after transfection, the cells were trypsinized and seeded to 10 cm dishes at 1×10⁶/dish density. The medium was changed the following day with 200 μg/ml of hygromycin B (ICN Biomedical, Inc. Aurora, Ohio) to select stable cell transformants.

Packaging and Preparation of Virion Stocks

The hygromycin resistant colonies which contained pHE700-lac in episomal form were trypsinized and 3×10⁶ cells were plated on a 10-cm dish. The next day when the cells were nearly confluent, 0.1 multiplicity of infection (MOI) helper virus in 1 ml of Opti-MEM was added to the dish. The viruses were allowed to adsorb to the cells for 3 hours at 37° C. in a humidified, 5% $CO_2$ incubator. The virus solutions were aspirated and 10 ml of DMEM with 10% of FBS was added and incubated for 2 to 3 days at 37° C. in a humidified, 5% $CO_2$ incubator. The medium containing cell debris was collected and centrifuged and supernate was used for virus titration and infection. For production of helper virus, 0.025 MOI helper virus was used.

Titration

The virus stocks were diluted in 100 μl Opti-MEM media and the $10^{-3}$ to $10^{-8}$ dilutions were used to infect confluent monolayers of E5 cells grown in 6-well plates. The viruses were allowed to adsorb to the cells for 3 hours at 37° C. in a humidified, 5% $CO_2$ incubator. The virus solutions were aspirated and washed with Hank's solution and overlaid with 2 ml DMEM containing 5% FBS and 0.3% methylcellulose and then placed at 37° C. in a humidified, 5% $CO_2$ incubator for 3 days. Plaques were visualized by staining with 1 ml of 0.5% crystal violet for 10 minutes. The plates were dried and the plaques were counted. The titers were determined as the plaque forming unit per milliliter (pfu/ml) from the number of plaques in a well times dilution factor. pHE700-lac mini-viral vector stocks were titered by infection of T98G cells in the condition as described above. One X-gal positive T98G cell assuming representing one infectious pHE700-lac virion and the titers were determined as blue cell forming unite per milliliter (bfu/ml) by the number of blue cells in a well times dilution factor.

In Vitro infection with pHE700-lac:

For in vitro infection, cultured human cells from different sources including a number of tumor cell lines were trypsinized, counted and seeded (at appreciate densities). When cells confluent, defective viral pHE700-lac was incubated with the cells at 3–10 MOI for 3 hours. The β-galactosidase activity was measured 24 hours later for in vitro infection.

Assays for β-galactosidase Activity

Two assays were used to detect β-galactosidase activity in pHE700-lac infected cells. For visualization of virions carrying lacZ gene, infected cells were rinsed with PBS on the second day following infection. The cells were then fixed for 5 minutes at room temperature in 2% Formaldehyde, 0.3% glutaraldehyde in Hank's Balanced Salt Solution (HBSS), and stained by incubating in a chromophore solution containing 0.1% X-Gal (5-bromo4-chloro-3-indolyl-B-D-galactopyranoside) (Promega), 5 mM $K_4Fe(CN)_6$ $3H_2O$, 5 mM $K_3Fe(CN)_6$, and 2 mM $MgCl_2$ in HBSS. Incubation continued at 37° C. until color developed (usually within 30 to 60 minutes). For quantity measurement of β-galactosidase activity, after 48 hours of infection, all cells were trypsinized and washed once in HBSS solution and 1.0×106 cells were resuspended in an ONPG lysis solution (0.45 mM O-nitrophenyl-b-D-galactopyranoside and 0.5% Nonidet P-40 in HBSS). Cell lysis were then incubated at 37° C. in a 5% $CO_2$ humidified incubator, and the optical density (OD) at 420 nm was taken 1 hour later.

Figure 3A:
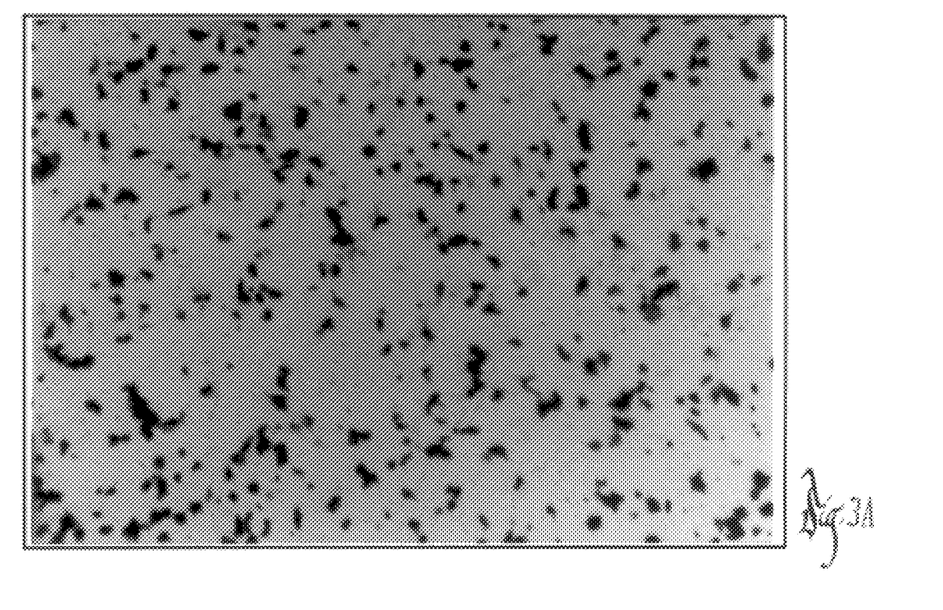
FIGS. 3(a)–3(c) are photographs depicting transfection and selection of E5 cells in culture after transfection with 1 µg of plasmid pHE700-lac in 10µl of Lipofection. The transfection was very efficient and excellent β-galactosidase gene expression was detected 24 hours later (FIG. 3A). E5 cells transfected with pHE700-lac and 48 hours later were placed into selection with 200 µg/ml of hygromycin. Six days (FIG. 3B) or 10 days (FIG. 3C) later these cells were then fixed and stained with X-gal.
Figure 3B:
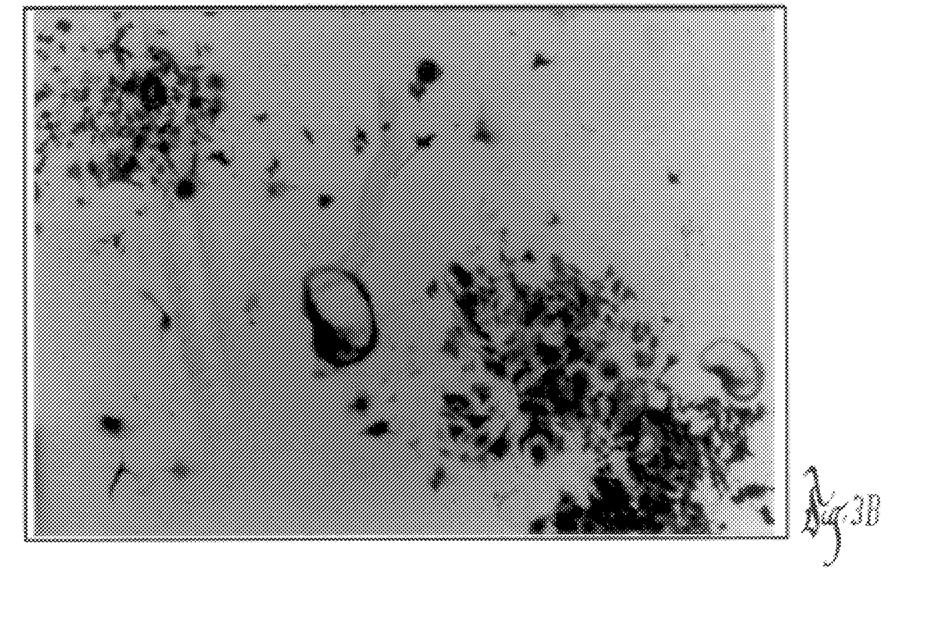
Figure 3C:
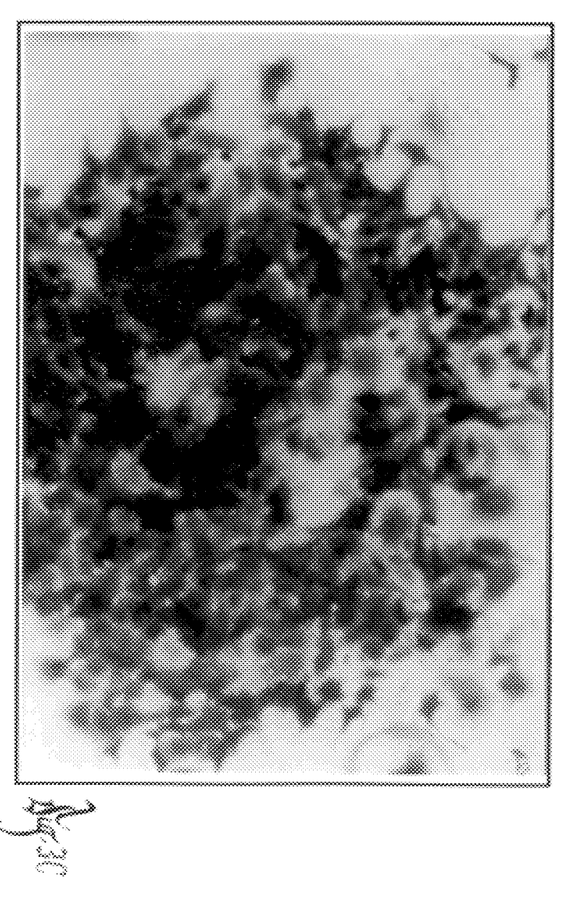
Figure 4A:
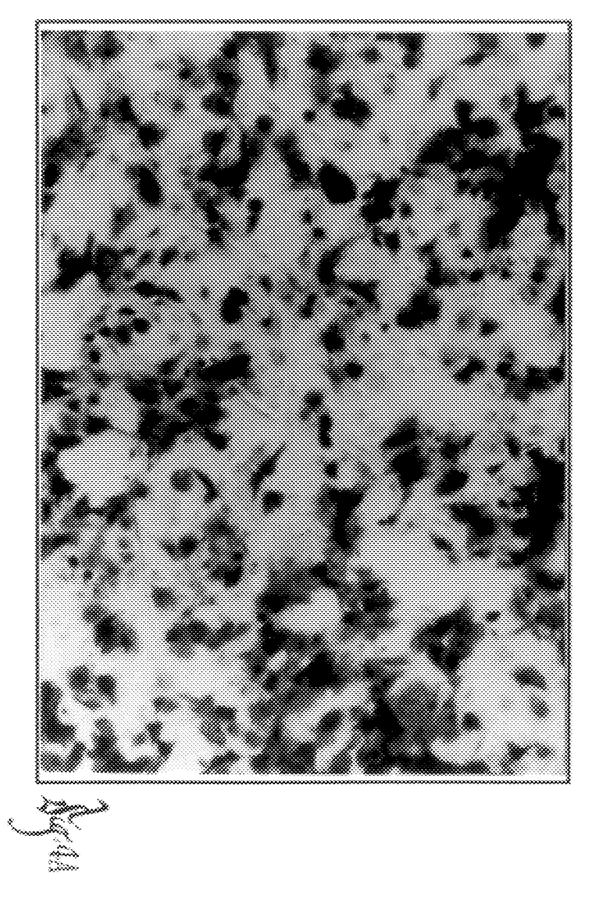
Figure 4B:
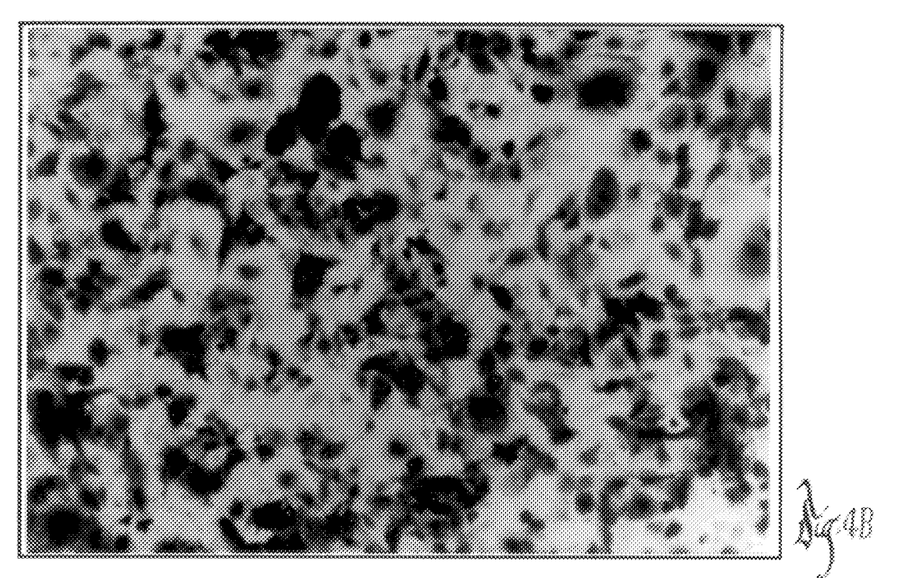
Figure 4C:
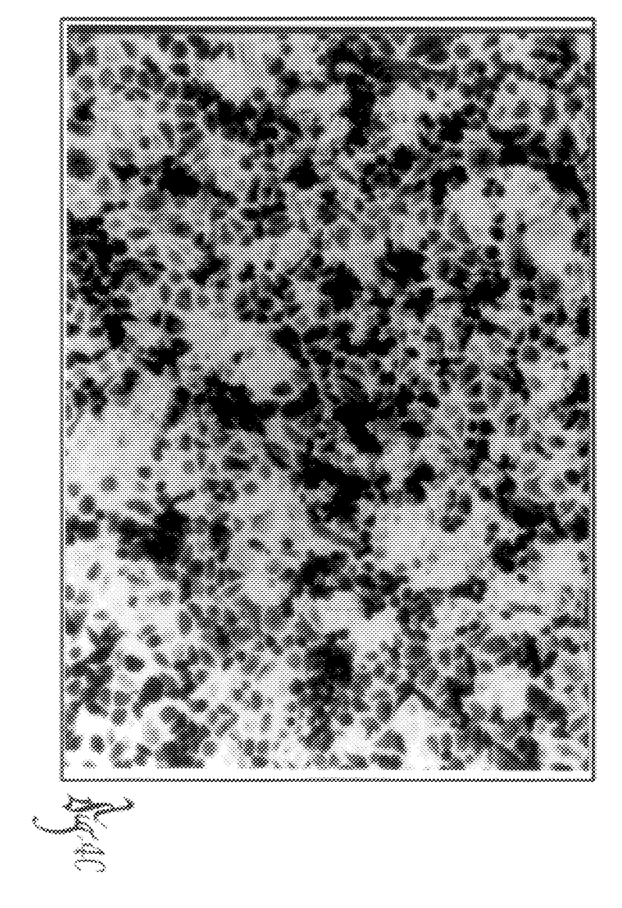

LacZ gene transfer was conducted with the pHE700 vector into human tumor cells. FIGS. 3 and 4 demonstrate a series of experiment with the pHE700 vector.

Additionally construction of Green Fluorescent Protein (GFP) containing pHE700 vector was also accomplished. This system allows for the efficient detection of HSV mini-vector mediated gene transfer in living cells.

FIGS. 3(a)–3(c) are photographs depicting transfection and selection of E5 cells in culture after transfection with 1 μg of plasmid pHE700-lac in 10μl of Lipofection. E5 cells were plated at 5×105 cells in a 6 well plate. Cell were then stained 2 days later with X-gal. The transfection was very efficient and excellent β-galactosidase gene expression was detected (FIG. 3A). E5 cells transfected with pHE700-lac and 48 hours later were placed into selection with 200 μg/ml of hygromycin. Six days (FIG. 3B) or 10 days (FIG. 3C) later these cells were then fixed and stained with X-gal. The selection demonstrates the ability of the plasmid to allow for the selection of cell colonies of strong expressing transfectants.

Herpes Mini-Vector Transduced Cells

E5 cells transfected and selected with pHE700 and then selected in hygromycin were used to generate Herpes viral stocks. The producer cells were infected with helper virus and the cells were allowed to undergo a progressive infection and lysis. The supernate was then collected and titered on target cells by determining β-galactosidase gene expression. This pHE700-lac virus stock was then used to infect VA13 human fibroblasts at a MOI of 3 (FIG. 4A), SV3 CRL 9.7 xeroderma pigmentosum fibroblasts at an MOI of 10 (FIG. 4B), IGROV human ovarian carcinoma cells at an MOI of 10 (FIG. 4C), a human glioblastoma multiform cells at an MOI of 10.

FIG. 4D. VA13, IGROV, SV3 CRL 9.7 were photographed at 10× magnification.

All cells were fixed and stained two days after infection. These results demonstrate very high level gene transfer and expression with this delivery system in normal cells, cells from a genetic syndrome patient, and cells from two different types of malignant cells.

What is claimed is:

1. A recombinant mini-viral Herpes Simplex Virus vector comprising:
   a replication origin, "ori S" from Herpes Simplex Virus;
   an Herpes Simplex Virus packaging sequence "a";
   an Epstein-Barr Virus nuclear antigen gene "EBNA-1"; and
   an Epstein-Barr Virus latent origin of replication "ori P".

2. The vector of claim 1 further comprising: procaryotic genes for propagation of said vector in E. coli.

3. The vector of claim 1 further comprising prokaryotic genes for Hygromycin resistance, or the eukaryotic gene MDR-1.

4. The vector of claim 1 further comprising a transcription unit for expression of a nucleotide sequence the expression of which is desired in a cell.

5. The vector of claim 2 wherein said E. coli genes include a col E1 ori gene.

6. The vector of claim 5 further comprising a selectable marker gene for propagation in E. coli.

7. The vector of claim 6 wherein said selectable marker gene is selected from the group consisting of an ampicillin resistance gene, kanamycin resistance gene, tetracycline resistance gene and zeocin resistance gene.

8. The vector of claim 3 wherein said Hygromycin resistance gene is flanked on one end with a promoter regulator region and on the other with a transcription termination signal.

9. The vector of claim 8 wherein said promoter is the Herpes Simplex Virus thymidine kinase promoter and said transcription termination signal is the Herpes Simplex Virus thymidine kinase polyadenylation signal.

10. The vector of claim 4 wherein said transcription unit comprises a foreign gene to be expressed, a promoter and a polyadenylation site.

11. The vector of claim 4 wherein said transcription unit comprises a gene with its native regulator elements, its exon and intron regions and its termination signal.

12. The vector of claim 4 wherein said nucleotide sequence is the cDNA which encodes Duchennes muscular dystrophy.

13. The transcription unit of claim 4 comprising a promoter selected from the group consisting of an inducible promoter, a tissue specific promoter and an artificial promoter enhancer.

14. The transcription unit of claim 10 wherein said promoter is selected from the group consisting of the cytomegalovirus promoter early promoter and the Rous sarcoma virus long terminal repeat, and wherein said polyadenylation site is the SV40 polyadenylation site.

15. The vector of claim 14 wherein said vector includes a multiple cloning site.

16. The vector of claim 15 wherein said multiple cloning site is the multiple cloning site depicted in FIG. 1.

17. A method for producing recombinant HSV/EBV viral particles comprising the steps of:
   (a) introducing into a helper cell line an HSV/EBV vector comprising the package cleavage signal sequence from HSV, a replication origin ori S from HSV, an EBNA-1 gene from Epstein-Barr Virus and an ori P gene from Epstein-Barr Virus;
   (b) growing said helper cell line in a cell growth medium; and
   (c) inducing virion propagation by introducing a complementing Herpes Simplex Virus ΔIE3 helper virus to said cell line so that recombinant HSV/EBV viral particles are produced.

18. The method of claim 17 wherein said helper cell line expresses the HSV IE3 gene, and said helper virus is a HSV ΔIE3 mutant.

19. The method of claim 17 wherein said vector further comprises:
   procaryotic genes for hygromycin resistance.

20. The method of claim 19 further comprising the step of:
   selecting for hygromycin resistance prior to inducing virion propagation.

21. A cell line transfected with HSV/EBV plasmid vector, said HSV/EBV plasmid vector comprising:

an Epstein-Barr Virus nuclear antigen gene, an Epstein-Barr Virus latent origin of replication, a Herpes Simplex Virus package cleavage signal, and a replication origin "ori S" from Herpes Simplex Virus.

22. The cell line of claim 21 wherein said cell line expresses an IE3 Herpes Simplex Virus gene and comprises a HSV helper virus.

23. The cell line of claim 22 wherein cell line expresses the Epstein-Barr virus EBNA-1gene.

24. The cell line of claim 22 wherein said helper virus is a IE gene deletion mutant which is complemented by said cell line.

25. The cell line of claim 24 wherein said HSV helper virus is a ΔIE3 mutant.

26. The cell line of claim 23 wherein said HSV/EBV plasmid vector omits the EBNA-1 gene.

27. A recombinant mini-viral Herpes Simplex Virus vector comprising:

a replication origin, "ori S" from Herpes Simplex Virus;

an Herpes Simplex Virus packaging sequence "A"; and a second viral sequence which allows the vector to be maintained in episomal form.

28. The vector of claim 27 wherein said second viral sequence is selected from the group consisting of Epstein-Barr virus, bovine papillomavirus and human papillomavirus.

29. The vector of claim 27 further comprising a reporter gene.

30. The vector of claim 27 further comprising a transgene.

31. The vector of claim 27 further comprising fusion genes.

32. The vector of claim 27 further comprising multiple genes.

33. A plasmid HSV mini-viral, said vector selected from the group consisting of pHE700; pHE750; pHE500, pHE550, pHE650; pHE400, and pHE450.

* * * * *